United States Patent [19]

Nussbickl

[11] Patent Number: 4,527,291
[45] Date of Patent: Jul. 9, 1985

[54] SAFETY GOGGLES, IN PARTICULAR FOR WORK USE

[75] Inventor: Walter Nussbickl, Wachendorf, Fed. Rep. of Germany

[73] Assignee: Uvex Winter Optik GmbH, Fürth, Fed. Rep. of Germany

[21] Appl. No.: 521,170

[22] Filed: Aug. 8, 1983

[30] Foreign Application Priority Data

Feb. 1, 1983 [DE] Fed. Rep. of Germany ... 8302644[U]

[51] Int. Cl.³ .............................................. A61F 9/02
[52] U.S. Cl. ......................................... 2/450; 2/451; 2/453; 351/115
[58] Field of Search ............... 2/450, 448, 449, 451, 2/453, 426, 439, 431; 351/115, 116, 121, 111, 113

[56] References Cited

U.S. PATENT DOCUMENTS 2,513,507  7/1950  Moeller ........................ 351/116 X
3,189,912  6/1965  Miller ........................... 351/115 X
3,212,102  10/1965  Muller .............................. 2/449 X
3,720,956  3/1973  Raschke ............................... 2/8

FOREIGN PATENT DOCUMENTS 1132355  6/1962  Fed. Rep. of Germany ...... 351/115
0527807  6/1955  Italy ..................................... 351/115

Primary Examiner—Peter Nerbun
Attorney, Agent, or Firm—Browdy and Neimark

[57] ABSTRACT

Safety goggles, particularly useful as work goggles, having temples disposed on and inclinable relative to a frame having lenses and side guards. In accordance with the invention, a protrusion which serves as a swivel bearing is mounted on each of the opposite side guards, and a swivel bearing appendage having a recess therein is adapted to be pressed onto the protrusion. The temple is hingedly connected to the swivel bearing appendage, whereby to permit pivotal movement of the temple relative to the swivel bearing appendage and thus to the goggle frame. The swivel bearing appendage is inherently elastic, permitting a portion of the swivel bearing appendage to grip the back surface of the side guard. A holder appendage portion of the temple may also grip the back surface of the side guard. The temple can have its angle of vertical inclination adjusted relative to the frame due to the angularly adjustable engagement of the swivel bearing appendage with the protrusion on the side guard, since the temple is moveable with the swivel bearing appendage.

12 Claims, 3 Drawing Figures

SAFETY GOGGLES, IN PARTICULAR FOR WORK USE

FIELD OF THE INVENTION

The invention is directed to safety goggles, in particular for work use, having temples disposed on and inclinable relative to a frame having side guards.

BACKGROUND OF THE INVENTION

In known safety goggles of this kind, tang-like appendages are provided at the side of the frame. The temples, in the position for supporting the goggles, have horizontal recesses over which the tangs fit. In order to have these recesses, the temples are widened on the outside in this area. A structure of this kind is not entirely satisfactory in terms of design. Furthermore, in previous safety goggles of this kind it was difficult to mount the temples on the frame, because either screws had to be actuated to accomplish this, or complicated sequences of movements had to be performed, making the assembly of the goggles labor-intensive and therefore expensive.

SUMMARY OF THE INVENTION

With the above considerations in mind, the object of the present invention is to provide safety goggles in which the inclinable temples are easy to attach and to change as needed, in which the swivel apparatus can be embodied in an aesthetically pleasing manner and can be manipulated comfortably, and in which a reliable, secure connection of the temples on the frame is assured.

This object is attained in safety goggles of the general type discussed hereinbefore in that a platelike protrusion serving as a swivel bearing is disposed on the side guard, and the associated temple fits over or around this protrusion, preferably such that it locks into place, with an appendage having a corresponding swivel bearing recess. An arrangement of this kind makes a relatively flat embodiment attainable, so that the swivel apparatus can be integrated into the design without difficulty. Goggles of this kind can furthermore be assembled easily and can therefore be manufactured at a favorable cost.

In a further embodiment of the invention it is provided that a holder appendage of the temple and/or of the swivel bearing appendage grips the side guard from behind in a form-fitting manner in the vicinity of the swivel bearing appendage, which is embodied as inherently elastic. As a result of this appendage which grips from behind, a particularly reliable, secure connection of the temple with the frame is attained. In order to attach or remove a temple, the swivel bearing appendage is swung back in an inherently elastic manner in the vicinity of the swivel bearing protrusion and thereby locks into place while returning to its initial position, the holder appendage simultaneously gripping the side guard of the frame from behind. In this manner not only is assembling the goggles facilitated, but unintentionally releasing the temples from the frame is prevented.

A hinge is preferably disposed between the swivel bearing appendage and the temple. In a preferred embodiment, the hinge is embodied in the holder appendage. Since the holder appendage in any event comes to rest on inside, the hinge is thus disposed in a position which is not only protected but is also advantageous in functional and aesthetic terms.

In structural terms, the embodiment is preferably effected such that a flush transition from the temple to the swivel bearing appendage is provided on the outside.

It proves to be advantageous that abutments which limit the angle of inclination and which engage recesses of the swivel bearing appendage are provided on the swivel bearing protrusion. These inclination-limiting abutments permit a free adjustment in terms of the inclination of the temples relative to the lenses within a predetermined angular range, yet they limit this range such that the temples are not capable under any circumstances of assuming a position which is unacceptable for practical use, such that they would have to be readjusted first before being used.

It is preferably provided that fluting is disposed on the bearing surfaces in contact with one another of the swivel bearing protrusion and the swivel bearing appendage. As a result of these fluted surfaces, the temples are held firmly in a desired angular position, yet on the other hand they are easily adjusted if required.

From the manufacturing standpoint it is particularly advantageous that a ring carrying the limiting abutments and/or the fluting can be mounted upon a swivel bearing plate which is fabricated integral with the frame, in order to serve as a mounting means for the swivel bearing appendage.

Further characteristics, advantages and details of the invention will become apparent from the following description of a preferred form of embodiment, referring to the drawings.

DESCRIPTION OF THE PREFERRED EMBODIMENT

Figure 1:
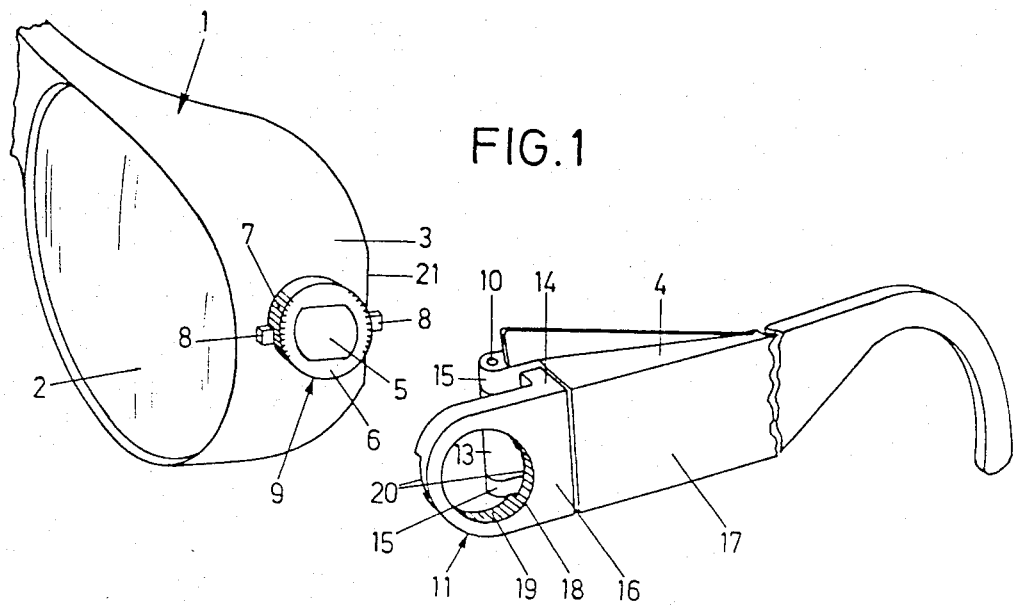
FIG. 1 is a perspective view of the frame and temples of the safety goggles according to the invention, seen with the temples not attached to the frame.
Figure 2:
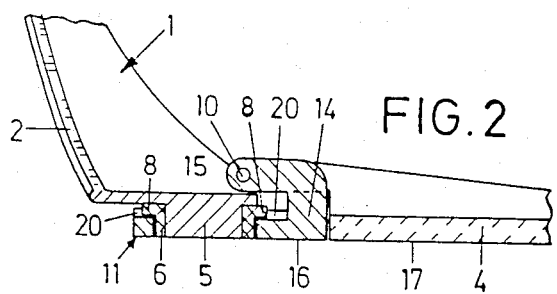
FIG. 2 is a horizontal section through the area of the hinge, in the position in which the goggles are used.

The safety work goggles shown in FIG. 1 include a frame 1 with lenses 2; the frame 1 has a side guard 3 embodied on each side. A temple 4 is articulated or pivotally mounted on each side guard 3.

A swivel bearing plate 5 is injection molded in one piece with the frame 1. The swivel bearing plate 5 is surrounded by a ring 6, which has fluted surface 7 and abutments 8 for limiting the angle of inclination of temple 4 relative to frame 1. Together, the swivel bearing plate 5 and the ring 6 comprise a swivel bearing protrusion 9.

Figure 3:
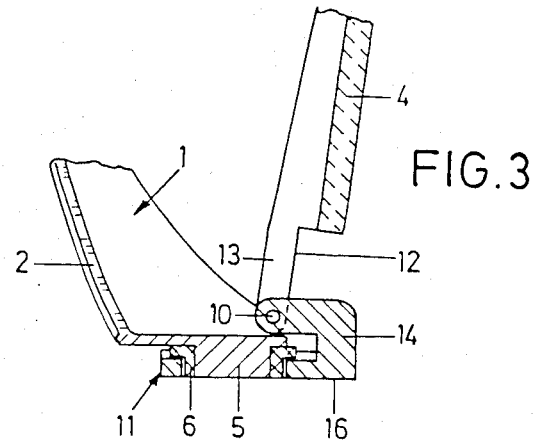
FIG. 3 is a sectional view corresponding to FIG. 2 of the end of the temple toward the hinge, showing the swivel appendage in the swung-out position.

Each temple 4 has a hinge 10 at one end, on which a swivel bearing appendage 11 is disposed in articulated fashion, to permit pivotal movement of the temple 4 relative to the swivel bearing appendage 11, as seen particularly in FIG. 3. The temple 4 is constructed so that it has a recess 12 on its end toward the hinge. The recess 12 is formed by a step in the temple 4 and by a holder appendage 13 which adjoins the step. One of the hinge elements of hinge 10 is defined by holder appendage 13 carried by temple 4. The swivel bearing appendage 11 has a shank 14 parallel to its body. The shank 14 carries hinge elements defined by eyes 15 of the hinge, which cooperate with the hinge element defined by holder appendage 13 of temple 4. The pin of hinge 10 passes through eyes 15 and through the hinge element defined by holder appendage 13. Because of this construction of the bearing, it is possible to move temple 4 pivotally relative to swivel bearing appendage 11 about the axis of hinge 10 so that the outer surface 17 of temple 4 is flush with the outer surface 16 of swivel bearing appendage 11.

The swivel bearing appendage 11 has a swivel bearing recess 18 having a fluted surface 19 on its inside. In the assembled state, the swivel bearing appendage 11 fits around the swivel bearing protrusion 9, whereupon the fluting 7 engages the fluted surface 19 of swivel bearing recess 18, so that on the one hand unintentional adjustment of the angle of inclination of the temples 4 about swivel bearing protrusion 9 is avoided, yet on the other hand an arbitrary angular adjustment of temple 4 relative to swivel bearing protrusion 9 can be accomplished without difficulty at any time.

Recesses 20 are embodied in the swivel bearing appendage 11, permitting a swiveling movement of the temple 4 within an angular range about the abutments 8 for limiting the angle of inclination of temple 4. The outer rims of the recesses 20 define the angular range of this movement.

To mount the temples 4, the front edge of the swivel bearing appendage 11 is placed against the swivel bearing protrusion 9 and pressed in. As a result, the swivel bearing appendage 11 is bent back because of its inherent elasticity, and the temple 4 can be pushed into place in the direction toward the lenses 2, whereupon the holder appendage 13 grips the rear edge 21 of the side guard 3 from the inside. After the operation of pushing the temple onto the protrusion 9 is complete, the swivel bearing appendage 11 locks into place over the swivel bearing protrusion 9, causing the swivel bearing protrusion 9 to engage the swivel bearing recess 18. All that is required to remove a temple is to lift the swivel bearing appendage 11 at its front edge and move it above the swivel bearing protrusion 9, making is possible to pull off the temple toward the back. On the other hand, it is assured that the temple cannot be released unintentionally, because a firm seating is attained as a result of the interaction between the holder appendage 13 gripping the frame 1 from behind and the elastic contact of the swivel bearing appendage 11.

In order to secure the ring 6 on the swivel bearing plate 5 such that it cannot be twisted, it may be provided that bores be disposed in the frame 1 to the side of the swivel bearing plate 5, the bores being engaged by corresponding tangs of the ring 6.

What is claimed is:

1. Safety goggles including temples disposed on and inclinable relative to a frame having lenses and side guards, comprising:

swivel bearing means defined by a platelike protrusion integrally formed on said side guards of said frame and including a ring member having abutments positioned opposite each other on the periphery of said ring member, said ring member being secured to the outer periphery of said platelike protrusion of said swivel bearing means;

swivel bearing appendage means connected to each of said temples, each of said swivel bearing appendage means being inherently elastic and having inner swivel bearing recesses for cooperative mating with said abutments on said ring member of said swivel bearing means, said recesses being adapted to lock said swivel bearing appendage means to said side guards of said frame, said swivel bearing appendage means being inclinable with respect to a plane perpendicular to said side guards of said frame;

said temples and said swivel bearing appendage means defining a subassembly and a portion of said subassembly gripping said side guards of said frame from behind in a form fitting manner to secure said subassembly to said side guard of said frame.

2. Safety goggles as defined in claim 1 in which a portion of said swivel bearing appendage means grips said side guard from behind in a form fitting manner.

3. Safety goggles as defined in claim 1 in which holder appendage means on each said temple grips said side guard from behind in a form fitting manner.

4. Safety goggles as defined by claim 1 in which said temple is hingedly connected to said swivel bearing appendage means.

5. Safety goggles as defined in claim 4 in which one of the hinge elements of the hinged connection is carried by said holder appendage means of said temple.

6. Safety goggles as defined by claim 1 wherein each said temple and said swivel bearing appendage means is movable relative to each other to a position in which their outer surfaces are flush with each other.

7. Safety goggles as defined by claim 1 wherein said abutments limit the inclination of each temple relative to the frame said abutments being mounted on said ring member for engagement with the recesses of the outer surface of said swivel bearing appendage means.

8. Safety goggles as defined by claim 1 wherein the outside surface of said ring member and the cooperation bearing surfaces of said swivel bearing appendage means are both provided with fluting.

9. Safety goggles as defined in claim 1 in which said ring means comprises a bearing plate integral with said frame.

10. Safety goggles as defined in claim 9 comprising separate ring means mounted on said bearing plate about the outer periphery of said bearing plate.

11. Safety goggles as defined in claim 9 or 10 in which said swivel bearing appendage means is adapted to be mounted on said ring means.

12. Safety goggles as defined in claim 9 or 10 in which the outer periphery of said ring means is fluted.

* * * * *